United States Patent [19]

Reenstierna

[11] 4,332,323

[45] Jun. 1, 1982

[54] DESTRUCTION DEVICE FOR INJECTION NEEDLES

[75] Inventor: Erik G. B. Reenstierna, Bjärred, Sweden

[73] Assignee: Konsivenior AB, Sweden

[21] Appl. No.: 261,198

[22] PCT Filed: Oct. 26, 1978

[86] PCT No.: PCT/SE78/00064

§ 371 Date: Jun. 26, 1979

§ 102(e) Date: Jun. 22, 1979

[87] PCT Pub. No.: WO79/00239

PCT Pub. Date: May 3, 1979

[30] Foreign Application Priority Data

Oct. 26, 1977 [SE] Sweden ................................. 772041

[51] Int. Cl.³ .................... B65D 85/00; A61M 5/32; B02C 19/12; B21D 7/00

[52] U.S. Cl. ................................. 206/365; 83/925 R; 225/93; 225/94; 225/104

[58] Field of Search ............... 206/366, 365, 359, 370, 206/571, 63.5; 225/93, 94, 102, 104; 83/925 R

[56] References Cited

U.S. PATENT DOCUMENTS

| | | | |
|---|---|---|---|
| 3,226,007 | 12/1965 | Thies et al. | 206/365 |
| 3,404,593 | 10/1968 | Arcarese et al. | 225/104 |
| 3,450,319 | 6/1969 | Ray et al. | 225/104 |
| 3,469,750 | 9/1969 | Vanderbeck | 225/94 |
| 3,736,824 | 6/1973 | Dunnican et al. | 225/93 |
| 3,796,359 | 3/1974 | Dick | 206/365 |
| 3,893,608 | 7/1975 | Koenig | 206/571 |
| 4,106,620 | 8/1978 | Brimmer et al. | 206/359 |
| 4,120,397 | 10/1978 | Neumann | 206/370 |
| 4,168,777 | 9/1979 | Gaskell et al. | 206/359 |

FOREIGN PATENT DOCUMENTS 2740335 3/1979 Fed. Rep. of Germany ...... 206/366

*Primary Examiner*—William T. Dixson, Jr.
*Attorney, Agent, or Firm*—Karl W. Flocks

[57] ABSTRACT

A device for the destruction of an injection needle has a sleeve (6; 14) in which the needle (3) mounted on a syringe may be inserted. The sleeve includes projections (9; 16) located beneath one another and projecting from opposite sides towards the path of movement of the needle within the sleeve. The projections are forced, by means of an actuator (5; 16) which is movably disposed in the sleeve and, as a result of engagement with the needle holder (4) is entrained in the movement of the needle, to move towards and into the path of movement of the needle so that the needle is bent or broken between these projections and is, in such a manner, rendered unusable.

8 Claims, 3 Drawing Figures

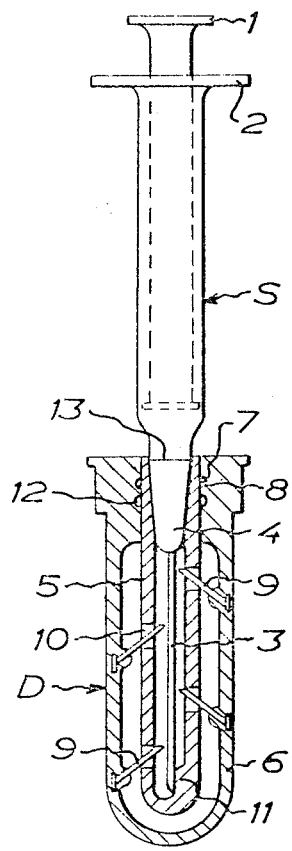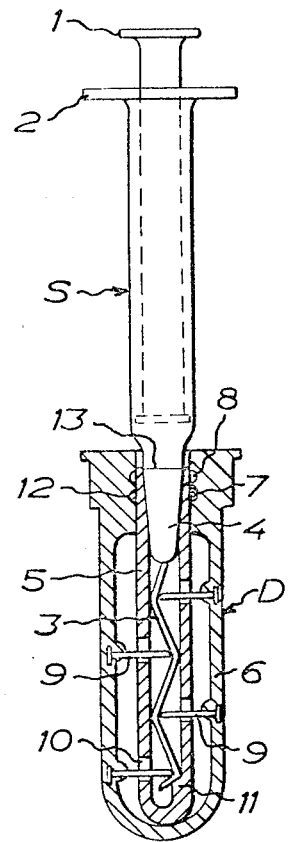

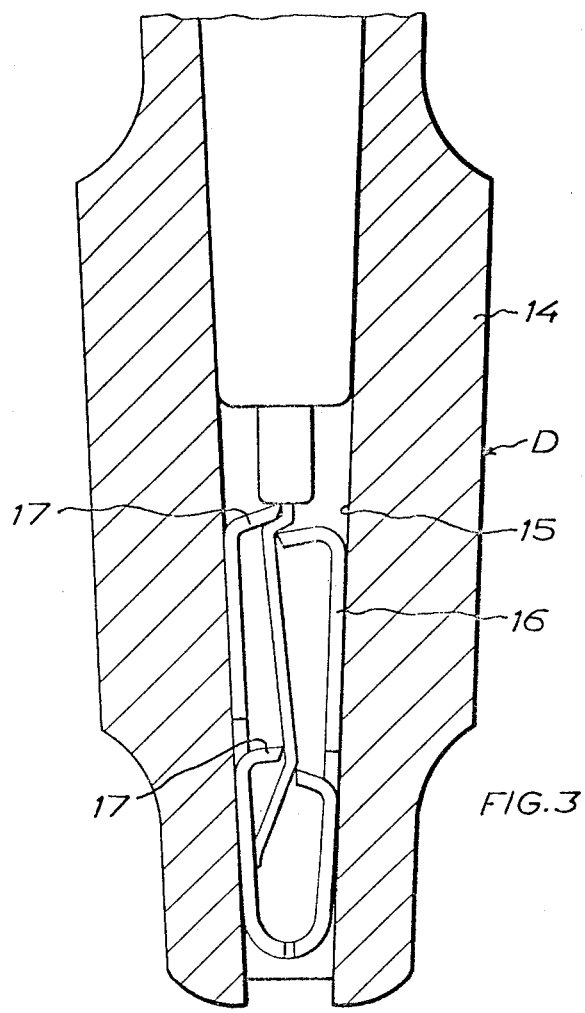

DESTRUCTION DEVICE FOR INJECTION NEEDLES

At the present time, not only large and complicated destruction installations which are under municipal supervision and take care of the hazardous waste from local hospitals but also simpler devices used in, for example, medical reception centres and by dentists are utilized for the destruction of different types of injection syringes in order that these shall not, after use, be capable of injury or infection and shall not be re-usable. A further large number of injection syringes are used in the home in the occurrence of different illnesses, for example by sufferers from diabetes and asthma. The patients are recommended or instructed, for the destruction of such injection syringes, to bend or possibly break the needle or cannula, for example with the protective cap of the needle, and to break or burn the syringe cylinder before these are deposited in the dustbin.

However, in particular this latter method of needle destruction recommended for patients in the home is highly unsatisfactory. Apart from the fact that the recommended or prescribed method is often disregarded completely as a result of forgetfulness or carelessness, this method requires the use of such force for breaking or bending the needle as many patients are unable to produce, with the result that the needle finds its way into the refuse bag in more or less original shape and can poke through the bag with the resultant risk of injury and infection. Furthermore, a needle which is not bent sufficiently may, after retrieval from the refuse bag, quite easily be straightened again by unlawful or unauthorized users who, alternatively, may, for purposes of re-use, break and sharpen the needle at the point of fracture, since relatively short needle lengths may also then be used.

The major aspect of the present invention is to obviate these disadvantages and thus to realize a needle destruction device which eliminates or, at least, considerably reduces the risks of injury or infection from the destroyed needle, as well as the risks of its reuse.

This aspect is achieved, according to the invention, by means of a device having the characteristics which are apparent from one or more of the accompanying claims.

The invention will be described in greater detail below with reference to the accompanying drawing, on which FIG. 1 shows one embodiment in the needle-protecting state, FIG. 2 shows the same embodiment in the needle-destruction state and FIG. 3 shows a further embodiment in the needle-destruction state.

FIG. 1 shows a conventional syringe assembly S which comprises an injection piston 1, an injection cylinder 2 and a needle or cannula 3, together with a needle destruction device D, according to the invention, disposed on the needle. The conventional conical needle holder 4 is accommodated with sliding fit in a corresponding conical upper, inner portion of a cylindrical inner sleeve 5 which is provided with a bottom and concentrically surrounds the needle. The inner sleeve is, in its turn, concentric with and connected to a cylindrical outer sleeve 6 also provided with a bottom. This connection is realized by means of a number of studs 7 on the outer side of the upper portion of the inner sleeve 5 and corresponding recesses 8, in which the studs 7 engage, on the inside of the upper, thickened portion of the outer sleeve 6. A number of steel blades 9 are fixedly retained below the upper portion of the outer sleeve 6 in the inner wall of the outer sleeve, the blades being disposed along two diametrically opposed vertical lines so as to form a zig-zag pattern. The blades 9 point obliquely towards the longitudinal axis of the sleeves 5 and 6 containing the needle 3, in a direction towards the needle holder 4, and extend through holes 10 in the inner sleeve 5 so that their tips terminate a distance from the needle 3. The length of the blades is greater than the perpendicular distance between the needle 3 and the anchorage points of the blades in the outer sleeve 6.

The sleeve 6 is made of yieldable material and may consist of a suitable thermoplastic, such that the blades 9 may be considered as being pivotally retained in the inner wall of the sleeve 6. The retention of the blades 9 in the inner wall of the sleeve 6 may be realized by, for example, injection moulding of the sleeve 6 around blades 9 disposed in the sleeve mould.

For unification of the sleeves 5 and 6, for example, the outer sleeve 6 with the blades 9 may be produced without a bottom and the inner sleeve 5 may be forced into the outer sleeve 6 through its bottom opening and be twisted until the blades 9 snap into the holes 10, whereafter a bottom is fixed, for example, by welding, to the outer sleeve 6.

The syringe assembly S and destruction device D may, in the combined state shown in FIG. 1, be sealed in a conventional manner, in a sterile package.

The function of the destruction device is as follows. When the syringe assembly S has been removed from its conventional, sterile transport package and withdrawn from the combination of the interconnected sleeves 5 and 6 which, prior to this withdrawal, also serve as a needle protector, the syringe assembly is ready for charging with the injection fluid and for performing the injection operation. When the injection operation has been carried out, the syringe assembly is reinserted into the combination of the sleeves 5 and 6 and, for destruction of the needle 3, the syringe assembly, together with the sleeves 5 and 6, is struck or pressed with the tip of the sleeve 6 against some object, for example, a table top. As a result, while the needle holder 4 is in engagement with the corresponding conical portion of the inner sleeve 5, the studs 7 are, because of the yieldability of the material of the sleeve 6, forced out of the recesses 8 and the inner sleeve 5 moves towards the bottom of the outer sleeve 6. Durng this movement, the blades 9 are forced to pivot downwardly by the defining walls of the holes 10 and are gradually moved into engagement with the needle 3 in order finally to bend the needle, or, if the needle is of brittle material, break it between them by the leverage effect on the needle. Thus, one blade tip serves as a fulcrum while the bending operation is effected by means of the adjacent blades.

It is possible, in order to realize as short a straight needle tip portion as possible, to provide the inner sleeve, as is shown on the drawing, with an inwardly projecting abutment 11 at its lowermost portion, this abutment serving as a stop when the bending operation is effected on the needle by means of the lowermost blade.

Preferably, provision should be made to allow for so much freedom of movement for the inner sleeve 5 towards the bottom of the outer sleeve 6 that the blades 9, during the impression of the inner sleeve 5 in the outer sleeve 6, may pivot somewhat past the position where they make an angle of 90° with the needle 3 such that retraction of the syringe assembly and thereby of the needle from the sleeve 5 is rendered more difficult. Moreover, the inner diameter of the inner sleeve 5 should preferably be such that the needle 3 is, during its movement, clamped beween the blade tips and the inner wall of the sleeve 5 so that the needle is flattened at the points of contact with the blade tips.

A second series of recesses 12 is provided beneath the recesses 8 for indicating a sufficient impression of the inner sleeve 5 in the outer sleeve 6 and, thus, for indicating the completion of the contemplated bending of the needle 3. The studs 7 snap into these second recesses 12 when the above-mentioned sufficient impression has been realized.

In order to prevent impression of the inner sleeve 5 and needle 3 such a distance into the outer sleeve 6 that the blades 9 relax their grip on the bent needle 3, the inner sleeve 5 may "bottom" in the outer sleeve 6 at a blade position where the contemplated bending has been achieved.

After bending or breaking of the needle 3, the syringe cylinder 2 with the piston 1 may, in a conventional manner, be broken away from the needle holder 4 at an indication of fracture 13 provided for this purpose. Otherwise, the syringe cylinder may be withdrawn from the holder 4, depending upon whether the syringe is integrally designed with the needle holder (that is to say if the syringe is of the singleuse, disposable type), or if the cylinder and piston of the syringe are intended for re-use and have a releasable connection with the needle holder 4.

The bent or broken needle 3 is now in safe keeping in the sleeves 5 and 6 and cannot cause injury. Attempts to separate the sleeves 5 and 6 would meet with great difficulty and would be of no use to unlawful or unauthorized users, since the needle is bent or broken into unusable short lengths.

FIG. 3 shows an alternative embodiment of the destruction device according to the invention in the needle-destruction position. The embodiment D comprises a sleeve 14 whose inner wall has a conically tapering portion 15. A U-shaped strip 16 of relatively resilient material, such as plastic or metal, is inserted in the sleeve, the outer, bottom surface of the strip being turned to face in the direction of taper of the portion 15. The shanks of the U-shaped strip have projections 17 pointing towards each other, an arrangement which may be realized by inward bending of portions of the shanks of the strip 16. When the forward portion of the syringe is inserted in the sleeve (the U-shaped strip being in an upper position in the portion 15 and ready to receive the needle between its shanks), the U-shaped strip 16 is forced and entrained by means of the needle holder in the direction of taper of the portion 15, as a result of which the shanks of the strip 16 are forced in a direction towards each other in the conical portion 15 so that the projections 17 grasp and gradually bend or break the needle of the syringe between them, as shown on the drawing.

The conically tapering inner portion 15 need not have an axis of symmetry, as shown in FIG. 3, but may be formed by a wall of the sleeve 14 parallel to the path of movement of the needle, and an opposing wall inclined with respect to the first wall. In such a case, only those projections 17 which are located on the shank of the U-shaped strip 16 adjacent the inclined wall will move in the transverse direction of the needle.

I claim:

1. Device for the destruction of the injection needle of an injection syringe, characterized by a sleeve (6; 14) in which the injection needle (3) may be inserted and which is provided, in its interior, with spaced apart elements (9; 17) in the longitudinal direction of the sleeve and projecting from opposite directions towards the intended path of movement of the needle in the sleeve, and members (5; 16) movable with respect to the sleeve in the longitudinal direction thereof and disposed, during their movement, to influence at least one of said elements in such a manner that this moves towards and into the path of movement of the needle.

2. Device according to claim 1, characterized in that said influencing members (5; 16) are provided with means for engagement with the needle holder of the injection syringe.

3. Device according to claim 1 or 2, characterized in that the elements (9) or some of them are, at their one end, pivotally anchored in the inner wall of the sleeve (6) and that the influencing members (5) are disposed to pivot the elements (9) beyond a position where they make a right angle with the longitudinal axis of the path of movement of the needle, for the purposes of hindering withdrawal of the bent needle from the sleeve (6).

4. Device according to claim 1, characterized in that said influencing member consists of a second sleeve (5) disposed within the first sleeve (6), and through whose side wall the elements (9) project towards the path of movement of the needle.

5. Device according to claim 4, characterized in that the second sleeve (5) displays one position in which it is in engagement with the first sleeve (6) which engagement is releasable by the exercising of force on the second sleeve (5) in the insertion direction of needle (3).

6. Device according to claim 5, characterized in that studs (7) are disposed, for said engagement, on the outer side of the second sleeve (5), and first recesses (8) in the inner side of the first sleeve, which first sleeve consists of a yieldable material.

7. Device according to claim 6, characterized in that second recesses (12) are provided in the inner side of the first sleeve (6) in the insertion direction of the needle ahead of the first recesses (8), which second recesses are arranged for engagement with the studs (7) for indicating the contemplated needle-bending or breaking and for interlocking the sleeves (5, 6).

8. Device according to any one of claims 1–3, characterized in that the sleeve (14) has an inner, conically tapering cavity (15) and that the influencing member (16) consists of a U-shaped resilient strip (16) which may be inserted into the cavity and support blades on its shanks, between which is defined the path of movement of the needle.

* * * * *